US009063045B2

(12) United States Patent
Srinivasan et al.

(10) Patent No.: US 9,063,045 B2
(45) Date of Patent: Jun. 23, 2015

(54) SAMPLE PRETREATMENT AND EXTRACTION

(71) Applicants: Kannan Srinivasan, Tracy, CA (US); Bruce Richter, Sandy, UT (US); Christopher A. Pohl, Union City, CA (US); Brett Murphy, Murray, UT (US); Brian Dorich, North Salt Lake, UT (US); SM Rahmat Ullah, Fremont, CA (US)

(72) Inventors: Kannan Srinivasan, Tracy, CA (US); Bruce Richter, Sandy, UT (US); Christopher A. Pohl, Union City, CA (US); Brett Murphy, Murray, UT (US); Brian Dorich, North Salt Lake, UT (US); SM Rahmat Ullah, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 56 days.

(21) Appl. No.: 13/958,810

(22) Filed: Aug. 5, 2013

(65) Prior Publication Data
US 2013/0316466 A1 Nov. 28, 2013

Related U.S. Application Data

(60) Division of application No. 13/175,699, filed on Jul. 1, 2011, now Pat. No. 8,507,292, which is a continuation of application No. 12/039,687, filed on Feb. 28, 2008, now abandoned.

(51) Int. Cl.
*G01N 1/18* (2006.01)
*G01N 1/34* (2006.01)
*B01D 11/04* (2006.01)
*B01J 20/04* (2006.01)
*B01J 20/10* (2006.01)
*B01J 20/14* (2006.01)
*B01J 20/26* (2006.01)
*B01J 20/32* (2006.01)
*G01N 1/40* (2006.01)
*G01N 30/72* (2006.01)
*G01N 30/96* (2006.01)

(52) U.S. Cl.
CPC .............. *G01N 1/34* (2013.01); *Y10T 436/10* (2015.01); *Y10T 436/255* (2015.01); *B01D 11/0492* (2013.01); *B01J 20/043* (2013.01); *B01J 20/10* (2013.01); *B01J 20/14* (2013.01); *B01J 20/26* (2013.01); *B01J 20/3236* (2013.01); *B01J 2220/46* (2013.01); *B01J 2220/66* (2013.01); *G01N 1/4022* (2013.01); *G01N 1/4044* (2013.01); *G01N 1/405* (2013.01); *G01N 30/7206* (2013.01); *G01N 30/96* (2013.01); *G01N 2001/4061* (2013.01)

(58) Field of Classification Search
None
See application file for complete search history.

(56) References Cited

U.S. PATENT DOCUMENTS

| 3,062,739 | A |   | 11/1962 | Crits |
| 4,235,715 | A | * | 11/1980 | Wiegert ........................ 210/670 |
| 4,874,520 | A |   | 10/1989 | Lee |
| 5,002,670 | A |   | 3/1991  | Pratt et al. |
| 5,562,963 | A |   | 10/1996 | Davis |
| 5,616,407 | A |   | 4/1997  | Fritz et al. |
| 5,785,856 | A |   | 7/1998  | Gleave et al. |
| 5,843,311 | A | * | 12/1998 | Richter et al. ............... 210/634 |
| 6,087,339 | A |   | 7/2000  | Hindsgaul |
| 6,391,204 | B1|   | 5/2002  | Russo, Jr. |
| 6,492,183 | B1|   | 12/2002 | Perman et al. |
| 6,616,893 | B1|   | 9/2003  | Pham |
| 2002/0004535 | A1 | | 1/2002 | Kotsuka et al. |
| 2003/0178370 | A1 | | 9/2003 | Fisk et al. |

FOREIGN PATENT DOCUMENTS

WO    WO 2006/095093 A1    9/2006

OTHER PUBLICATIONS

Enzweiler, J. et al. The separation of platinum, palladium and gold from silicate rocks by the anion exchange separation of chloro complexes after a sodium peroxide fusion: an investigation of low recoveries, 1995, Talanta, vol. 42 (10), pp. 1411-1418.*
AOAC Official Method 922.06, AOAC Official Methods of Analysis, 1996 AOAC International, 32.1.14.
AOAC Official Method 932.06, AOAC Official Methods of Analysis, 2006 AOAC International, 33.5.08.
AOAC Official Method 989.05, AOAC Official Methods of Analysis, 2006 AOAC International, 33.2.26.
Aveldano, Marta I., et al. Quantitative release of fatty acids from lipids by a simple hydrolysis procedure. Journal of Lipid Research 24:1101-1105 (1983).
Henion, M-C. Sold-phase extraction: method development, sorbents, and coupling with liquid chromatography. J. Chromatog. A 856:3-54 (1999).
Joshi, Vivek. Analysis of drugs of abuse from whole human blood, 2006, BIOforum Europe, retrieved from intenet site:http://www.millipore.com/bibliography.nsf/a73664f9f981af8c852569b9005b4eee/7f7197f9a63c40cf8525722c0052dd8c/$FILE/BioForumEurope1006.pdf.
Ridgway, K., S.P.D. Lalljie, R.M. Smith. Sample preparation techniques for the determination of trace residues and contaminants in foods. J. Chromatog. A 1153:36-53 (2007).

(Continued)

Primary Examiner — Robert Xu

(57) ABSTRACT

A method for pretreating and extracting a liquid sample by sorbing an aqueous liquid sample, including an organic analyte and an acid or a base, in a solid sorbent material, and at least partially neutralizing the acid or base by reaction with neutralizing ions retained on a support surface, and contacting the liquid sample-sorbed sorbent material at elevated temperature and pressure with an organic solvent to extract the analyte into said solvent, preferably in a vessel having an extraction chamber with a zirconium metal interior surface.

22 Claims, No Drawings

(56) References Cited

OTHER PUBLICATIONS

Skoog, D.A., D.M. West and F.J. Holler. *Analytical Chemistry, An Introduction*, Chapter 13, Saunders College Publishing, 6th ed., pp. 227-236.

(US EPA) Method 3545A, Pressurized Fluid Extraction (PFE). Jan. 1998.

US EPA, National Exposure Research Laboratory, Method 314.0, Determination of perchlorate in drinking water using ion chromatography, Nov. 1999.

Zhao, Z. F., et al. Development of a hydrothermal deposition process for applying zirconia coatings on BWR materials for IGSCC mitigation. Corrosion Science 49:830-843 (2006).

Aveldano, M.I., et al., Quantitative release of fatty acids from lipids by a simple hydrolysis procedure, 1983, Journal of Liquid Research, vol. 24, pp. 1101-1105.

\* cited by examiner

SAMPLE PRETREATMENT AND EXTRACTION

BACKGROUND OF THE INVENTION

Extraction of many samples for analysis requires the use of acid or base solvents. For example, acetic acid may be added during extraction of polychlorinated dibenzo-p-dioxins (PCDDs) and polychlorinateddibenzofurans (PCDFs) from a sample comprising of fly ash pretreated with hydrochloric acid. In this case, the extraction vessel and associated plumbing is exposed to hydrochloric acid and acetic acid. Some samples that require pretreatment with concentrated acids, bases or other chemicals such as enzymes (hydrolysis, saponification, etc.) prior to extraction so that the analytes of interest are available for extraction by organic or aqueous solvent systems. For example, extraction/analysis of lipids in some food samples is difficult since the lipids are complexed with carbohydrate or proteins. Disintegration of the sample with an acid and heat hydrolyzes the proteins and starch and liberates the fat to allow its easy extraction to release bound lipids. Typical samples analyzed by the acid hydrolysis method are baked and cooked foods such as cereals, bread, cookies, chips, mayonnaise, cooked meals, meat products and cheese products. Association of official Analytical Chemists International (AOAC) method 966.06 describes acid hydrolysis step for these samples followed by a liquid-liquid extraction (LLE) method called the Mojonnier extraction method. The lipids are extracted away from the acid and other matrix components using a specific ether based solvent and then the solvent is evaporated leaving the lipids available for gravimetric analysis or further analysis by GC/GC-MS after converting the lipids to the fatty acid ester form.

Inert materials like glass are often used to contain samples extracted with aggressive solvents, e.g. concentrated acid or base, to ensure complete solubility of the analytes of interest. The nature of glass prevents these extractions from being performed under high temperatures and pressures, and so these extractions are typically done at or near atmospheric pressure and with only slightly elevated temperatures. As a result, the extractions performed under these conditions take longer periods of time than those typical pursued with a pressurized solvent extraction technique. For example, extractions such as these are often performed in test tubes, beakers or other similar laboratory ware.

Accelerated solvent extraction methods performed by the ASE® system sold by Dionex Corporation are an accepted solid liquid extraction (SLE) method useful for extraction of many types of analytes. (As used herein the term "ASE" refers to an accelerated solvent extraction method such as performed by the ASE® system and to the system itself.) This method is described in U.S. Pat. No. 5,843,311 ("the '311 patent") and in EPA Method 3545. An automated system for performing the ASE method is described in U.S. Pat. No. 5,785,856. Other analytical methods include ones that pretreat samples with highly concentrated acids or bases (for example acid hydrolyzed samples with 8 M HCl).

Exposure to the acid in acid hydrolyzed samples can result in problems with existing instrumentation. For example, stainless steel components of the Dionex ASE® systems may be attacked by the acids particularly at the high temperatures (e.g. from 40° C. to 200° C.) employed during extraction, to blacken the stainless steel components is observed with the cell, tubing, filters and frits. In some extreme cases there is also clogging of the tubing and associated static valve failures. The above failures can affect robust system operation. Some of the above issues could be addressed in certain cases by cleaning the filters and frits by sonication or cleanup with concentrated nitric acid on a frequent basis or by replacing the components. These treatments can be cumbersome and could require aggressive reagents or they are expensive adding to the overall cost of the analysis. Similarly, when pursuing extraction with other aggressive solvents or sample conditions such as a caustic containing sample, the stainless steel components are affected.

A specific example of pretreatment prior to extraction is the pretreatment of food samples with either acid (hydrolysis) or base (saponification) prior to extraction with an organic solvent to determine lipid content. With hydrolysis, the samples are typically mixed with HCl (8 M) for 30-60 minutes at 70-80° C. After this, a couple of procedures can be followed. The liquid sample can undergo direct liquid-liquid extraction with a water immiscible solvent such as diethyl ether (Mojonnier Method AOAC Intl. Methods 989.05). Alternatively, the liquid sample can be mixed with combinations of diatomaceous earth and sand and then extracted by organic solvents (technique used by Foss and Buchi) or the liquid sample can be passed through a special filter paper (modified Rose-Gottlieb Method AOAC Intl. Methods 922.06, 932.06). Extraction of the filter paper provides the amount of fatty acids or lipids in the sample. In the case of saponification, the samples are usually acidified to protonate the fatty acids followed by liquid-liquid extraction with a water immiscible solvent to obtain the fatty acids (Schmid-Bondsynski-Ratzlaff Method).

The extraction of the sample, whether it is liquid-liquid extraction (LLE) or solid-liquid extraction (SLE), can be very time-consuming and can require large amounts of solvent. Very little automation exists (the Foss and Buchi apparatus are called automated Soxhlet extraction but still require 2-4 hours). Both Foss and Buchi use a mixture of diatomaceous earth (Celite) and sand to mix with the hydrolyzed samples. This mixture is then washed thoroughly with water to remove the HCl. After the water washing, the solid sample is placed in an automated Soxhlet extraction apparatus and extracted with hexane or petroleum ether for 2-4 hours. The construction of their apparatus is glass (inert), but the adsorbent used does not change the pH of the liquid extract or hydrozylate.

The use of materials such as zirconium, tantalum, hafnium, ceramics, Hastelloy, Inconel, etc. is known for use in inert valves, reactors and crucibles use for the digestion of materials. Companies such as Flowserve use titanium, Hastelloy, Inconel, zirconium and other metals and alloys in valves and valve parts. Tantaline puts a coating of tantalum on the surface of metallic parts to improve their corrosion resistance. Companies such as Evans offer zirconium or zirconium alloys as crucibles. There are also reports of using ceramics or "super alloys" for the lining of large scale reactor vessels.

The use of ion exchange materials for neutralizing acids and bases are known. (See U.S. Pat. Nos. 3,062,739 and 5,002,670.) Typically with acids anion exchange materials are used to remove the acid. In the lipid analysis case the use of anion exchange materials affects the recovery of the fatty acids since the acids tend to be retained by the anion exchange materials.

SUMMARY OF THE INVENTION

In one embodiment of the invention, a method is provided of pretreating and extracting a liquid sample including an organic analyte. The method comprises (a) sorbing an aqueous liquid sample including an organic analyte and an acid or a base in a solid sorbent material, and at least partially neutralizing or precipitating said acid or base by reaction with neutralizing ions retained on a support surface, and (b) contacting the liquid sample-sorbed sorbent material with an organic solvent to extract said analyte into said solvent.

In another embodiment, a method is provided of extracting organic analytes from a liquid sample in a solid matrix. The method comprises extracting the organic analyte in an organic solvent at an elevated temperature and pressure in a vessel having a zirconium metal interior surface.

In a further embodiment, a device is provided for pretreating and extracting a liquid sample, including an organic analyte. The device includes a housing defining an extraction chamber, and a solid sorbent material and neutralizing ions retained on a support surface, the sorbent material and neutralizing ions being disposed in the extraction chamber.

In another embodiment, an extraction device is provided for use in accelerated solvent extraction. The device includes a vessel with an interior wall defining an extraction chamber, said interior wall being formed of zirconium metal.

DETAILED DESCRIPTION OF PREFERRED EMBODIMENTS

In one embodiment of the present invention, an aqueous liquid sample including an organic analyte and an acid or a base is sorbed (i.e., absorbed and/or adsorbed) in a solid sorbent material. The acid or base is at least partially neutralized by reaction with neutralizing ions retained on a support surface. As used herein, the term "neutralizing ion(s)" includes ions which, (a) when contacted with an acid or base form a salt or (b) when contacted with matrix ions including an acid or a base in the sample, react to form a precipitate with the matrix ions. Thereafter, the liquid sample-sorbed sorbent material is contacted with an organic solvent to extract the analyte into the solvent. The support surface for the retained ions may be on the solid sorbent material or may be on an independent material such as ion exchange resin.

Such organic analyte-containing samples for use in the methods of the present invention are described in the '311 patent and in EPA method 3545.

As used herein, the combination of the solid sorbent material and neutralizing ions retained on a support surface are referred to as a "sorbent/neutralizer agent."

As used herein, unless otherwise indicated, the term "organic analyte" refers to the analyte in an original sample, or to the form of the analyte as pretreated prior to sorption, or as sorbed. Thus, if the original sample is pretreated with an acid or base, such as acid treatment to hydrolyze lipids in a sample, the term "organic analyte" includes the hydrolyzed lipids. Similarly, unless otherwise indicated, the terms "sample" or "liquid samples" encompass the original sample, the form of the sample as pretreated prior to sorption, or as sorbed.

To perform the methods of the present invention, a device is provided suitable for pretreating and extracting a liquid sample including an organic analyte. The device includes a housing defining an extraction chamber with suitable ports, and a solid sorbent material and neutralizing ions retained on a support surface. Both the sorbent material and neutralizing ions are disposed in the extraction chamber. In one embodiment, the support surface is on the sorbent material.

Suitable sorbent materials include diatomaceous earth, available from various vendors such as Celite Corporation, J. T. Baker, and Dionex Corporation; aluminum silicate, available as a commercial product called Stardust; and sodium polyacrylate. Preferably, the sorbent material is capable of sorbing substantially all of the water in an aqueous liquid sample.

The invention will first be described with respect to neutralizing agents that form a salt. In one embodiment of a sorbent/neutralizer agent, the support surface retaining the neutralizing ions is on the sorbent material, itself. One material of this type is referred to as an "entrapped sorbent/neutralizer agent." Here, a sorbent such as diatomaceous earth is loaded by contact with an acid or base solution or precipitating reagent defined hereinafter and at least partially dried to a sufficient extent to be highly sorbent, e.g. with an aqueous liquid content less than 5% by weight. The neutralized ions are entrapped in the sorbent by retention on the surface of the dried material. Thus, the dried material which serves as a sorbent/neutralizer agent which sorbs the liquid sample and the acid or base in the sample matrix is neutralized. For example, if the sample liquid contains concentrated acid, then the sorbent/neutralizer agent has entrapped base in it so that a salt is formed with the acid which is absorbed with the water in the aqueous liquid sample. It is advantageous to use sodium carbonate for this application since the neutralized product with the acid would be sodium chloride and carbonic acid, (carbon dioxide dissolved in water which should bubble out). A base entrapped sorbent/neutralizer agent using sodium hydroxide can also be used in place of the $Na_2CO_3$ entrapped material as described here. This embodiment does not add water to the system. Also, an entrapped sorbent/neutralizer agent does not require the use of an exchange resin material, e.g., cation-exchange material for neutralizing concentrated acid in a sample. This is advantageous in that cation-exchange material may interact with phenols in samples such as from soil, leading to diminished recovery of some samples.

In another embodiment of a sorbent/neutralizer agent, a sorbent material comprises a charged solid support such as a polymer including charged moieties on the polymer chain. Here the neutralizing agents are counter ions to the charged moieties electrostatically bound thereto. Suitable sorbent/neutralizing agents of this type include poly(acrylic acid) and copolymers there of, e.g. sodium polyacrylate, a partial sodium salt cross-linked, graft-poly(ethylene oxide), sold by Sigma Aldrich (P/N 432784).

In another embodiment of the invention, the neutralizer portion of the sorbent/neutralizer agent is an ion-exchange resin in the extraction chamber disposed separate from or mixed in the sorbent material. For example, neutralizing ions may comprise exchangeable ions on ion-exchange support media which form a salt in the acid or base in the sample. To neutralize acid in the sample, a cation-exchange resin, e.g., in sodium form, may be used as a separate component in combination with water-sorbent material such as diatomaceous earth. Here, the cation-exchange resin neutralizes the acid to produce sodium chloride which, along with water from the sample, is absorbed by the diatomaceous earth.

Suitable embodiments of neutralizing ions retained on a support surface are ion exchange moieties on cation exchange media including Amberlite IR120 in sodium form, Amberlite IR 122 in sodium form, Amberjet UP1400 in hydronium form (which can be converted to sodium form), Dowex 50WX8-400 in hydronium form (which can be converted to sodium form) or any other similar resin, suitably with a capacity of 1 to 5 meq/g, preferably 2 to 3 meq/g. Suitable embodiments of anion exchange materials are Dowex Marathon 550 A (OH) type 1, a strong base anion exchange styrene-DVB based gel, Amberlite IRA 67 and the like with a capacity of 0.5 to 5 meq/g, preferably 1 to 3 meq/g.

The sample-sorbed sorbent, in effect, permits a true SLE (solid-liquid extraction) platform. One such extraction platform is accelerated solvent extraction described in the '311 patent and in EPA method 3545, incorporated herein by reference. Such extraction uses elevated temperatures, e.g., from 40° C. to 200° C., more typically from 80° C. to 150° C., and elevated pressures of at least 100 psi, and typically from 1000 to 1500 psi or higher but below supercritical conditions.

As set forth above, the acid or base, in dilute or concentrated form, may be present in the liquid sample as recovered. Also, it may be added in pretreatment of the liquid sample. For example, concentrated acid may be added to liquid sample to hydrolyze lipids in the sample for analysis of the hydrolyzed lipids, referred to herein as the "drain method." Two layers are formed due to a density difference. The lipid layer after acid hydrolysis has a lower density than the concentrated aqueous acid layer. This difference in density causes a lipid layer to form on top of the aqueous acid layer. In this embodiment, a substantial portion of the lipid layer is removed from the aqueous acid layer and is sorbed by the sorbent substantially free of the acid in the acid layer. This lowers the acid strength in the sorbent for increased recovery, lowers analysis costs and permits smaller-sized devices or cells to be used.

Another embodiment of the invention relates to an extraction device for use at elevated temperatures and pressures, particularly one which may be used in the presence of corrosive liquids such as acids or bases, particularly concentrated acids or bases. The interior surface of the extraction chamber of such devices should be resistant to acids, bases, and organic solvents at elevated temperatures and pressures, such as used in accelerated solvent extraction as described in the '311 patent. It has been found that zirconium offers excellent resistance to many strong acids, including nitric acid, hydrochloric acid, and high concentrations of concentrated sulfuric acid as well as most organic acids. This makes zirconium a preferred metal for the interior wall or surface of an extraction chamber and valves such as under elevated temperatures and pressures such as used in accelerated solvent extraction. Zirconium also is particularly effective in systems of the foregoing type which utilize a sorbent/neutralizer agent to sorb an aqueous or liquid sample including an organic analyte and an acid or a base, such as an aqueous liquid sample which has been treated with concentrated acid to hydrolyze organic components such as lipids.

As set forth above, the neutralizing ions can also be ions on the solid surface that react with the acid or base to form a precipitate with matrix ions in the sample. Here, precipitation removes potentially interfering matrix ions. This type of removal is used in titrimetry and in chromatography applications. For example in U.S. EPA method 314.0 while analyzing for drinking water by ion chromatography the presence of high concentration of chloride and sulfate may interfere with analysis of low levels of ions such as perchlorate. In this approach an ion exchange resin in the silver form is used to remove the high concentrations of chloride by precipitation. Similarly, a cation exchange resin in the barium form can be used to remove the high concentrations of sulfate. These and other precipitation methods could be used in the present invention. Pretreatment by combining ion exchange medium with neutralizing ions in the appropriate form on a support surface to form a precipitate of the matrix ions and sorbent is useful for extraction applications according to the invention.

For example, a cation exchange resin phase in the silver form in conjunction with diatomaceous earth would be useful for removing the chloride from hydrochloric acid by precipitation, and the residual aqueous phase can be absorbed by the diatomaceous earth absorbent.

In another variant of this approach, an appropriate precipitating reagent could be entrapped in an absorbent, such as diatomaceous earth, and a similar reaction would proceed along with absorption of the residual aqueous phase. As defined herein, a precipitating reagent is a salt or other reagent including a precipitating moiety which, when contacted with an acid or base, forms a precipitate. For example, the diatomaceous earth could be soaked with a precipitating reagent comprising silver nitrate or silver chromate solution and dried to entrap the silver nitrate or silver chromate as a solid material in the diatomaceous earth sorbent. Here, the precipitating moiety is silver. The silver nitrate or silver chromate entrapped diatomaceous earth when exposed to high levels of chloride in an aqueous phase would precipitate the chloride ions as silver chloride any residual aqueous phase would be absorbed by the diatomaceous earth. Titration methods of the prior art, for example Chapter 13 in Analytical Chemistry by D. A. Skoog, D. M. West and F. J. Holler, list the various species that could be determined by precipitation method, and the same list of ions could be removed as per the present invention. The silver form ion exchange material or the silver salt entrapped diatomaceous earth is suitable for removing a variety of matrix ions such as chloride, bromide, iodide, thiocyanate and the like. Similarly, a barium form cation exchange material or the barium salt entrapped diatomaceous earth is suited for removing matrix ions such as sulfate and iodate.

Suitable ion exchange materials for the above precipitation application could be prepared from commercially available ion exchange resins by pumping in the appropriate reagent to convert it into the required form. Such methods are well known in the prior art. For example a cation exchange resin in the hydronium form could be converted to the silver form by pumping in a reagent such as silver nitrate solution. The resin is washed with DI water and is ready for use as per the present invention. It is also possible to combine two or more different resin types to facilitate precipitation of two or more different matrix ions and the residual aqueous phase is absorbed by the diatomaceous earth absorbent. For example when the matrix comprises of chloride and sulfate then a combination of cation exchange resin in the silver form and in the barium form would be used in conjunction with the diatomaceous earth.

Standard liquid-liquid extractions (LLE) are common methods of extracting samples after pretreatment with acids or bases. LLE uses large amounts of organic solvents and are very time consuming. There is little automation, so the labor costs are high. Basically, embodiments of this invention convert LLE into solid-liquid extraction (SLE) by mixing the liquid pretreated sample with the sorbent/neutralizer agent neutralizes the acid or base and sorbs the water thereby converting the liquid sample into a sample entrapped in a solid matrix. This mixture can then be extracted using any solid-liquid extraction technology including accelerated solvent extraction, sonication, Soxhlet, automated Soxhlet, etc.

SLE according to the present invention allows the elimination of tedious and time consuming liquid-liquid extractions. Liquid samples (whether pretreated with acids or bases or not) can be mixed with a unique sorbent/neutralizer agent and then undergo solid-liquid extractions. SLE are more predictable and easier to automate than LLE processes. LLE processes often use dangerous and flammable solvents such as diethyl ether while this new process uses safer solvent such as hexane. The use of zirconium allows the use of acidic or basic solvent systems for extraction. Thus, samples that have undergone pretreatments with acids (e.g., hydrolysis) or bases (e.g., saponification) to be extracted under SLE conditions with solvents such as hexane. When used in conjunction with technologies such as ASE, savings in extraction time, labor, and solvent usage can be realized.

The following non-limiting examples demonstrate the present invention for ion chromatography systems.

Example 1

In this example, the organic analyte sample undergoes a pretreatment with acids or bases prior to extraction, specifically hydrolysis with HCl. The sample is mixed with 10 mL of 8 M HCl in an appropriate glass or plastic container. The sample is heated at 80° C. for 60 min. After the hydrolysis, the liquid sample is mixed with the correct quantity of the sorbent/neutralizing agent to sorb the water and to partially neutralize the acid. The resulting sample is loaded into the appropriate size of cell, e.g. an ASE® Standard cell sold by Dionex Corporation, using loading procedures set forth in the '311 patent. The loaded cell is capped and placed in the ASE system of the '311 patent for extraction under the appropriate conditions (hexane at 100-125° C. and 1500 psi are common conditions). After the process, the liquid extract can be analyzed gravimetrically or by chromatographic or spectroscopic techniques to obtain the lipid or fatty acid content.

Example 2

This Example describes the sample preparation and extraction of pretreated acidic food sample for gravimetric lipid determination. In this example a cation exchange resin in sodium form and diatomaceous earth used for the purpose of neutralization and absorption of acidic sample matrix prior to solvent extraction in ASE.

A cation exchange resin was obtained from Rohm and Hass Amberlite IR-12-Na cation exchange resin (Na-form) and was oven dried when the moisture content was above 18% to achieve roughly 15±3%. Drying ensures that the resin would not allow water to permeate out of the resin and into the solvent used during extraction.

A) Acid Hydrolysis of Food-Procedure for Gravimetric Determination:

The food samples (usually 2 g) were weighed out in a 40 mL (Dionex Corporation, P/N 048783). A 2 mL ethanol was added and the contents were mixed. Finally 10 mL of 8M HCl was added and the contents were mixed thoroughly. Hydrolysis proceeded for 40 min at 70-80° C. with constant shaking (as described in AOAC method 996.06). The acid hydrolyzed samples were cooled to room temperature.

B) Sample Preparation Procedure for ASE:

The extraction of food samples were done in a 100 mL extraction cell. The bottom cell end cap was fixed and a filter was inserted. A plug (about 5-6 g) of resin was added at the bottom of the cell. A 16 g of ASE Prep DE (Dionex, P/N 062819) was taken into a mortar and lightly grinded. 30 g of dried resin from above was added into the mortar and mixed well by lab pestle. The combination of the ASE Prep DE and the resin is termed here as the sorbent/neutralizing agent and is used in this example to neutralize the concentrated acid and to absorb the residual salt and water. The acid hydrolyzed sample was added over this mix evenly in mortar. The hydrolysis sample bottle was rinsed with 1-2 mL portion of ethanol and petroleum ether to rinse out the residual sample into the mortar. The whole mass was mixed by pestle and also to break the clumps. This mixture was loaded into the same 100 mL cell containing the cellulose filter and resin. Another plug (about 4-5 g) of resin was added to top off the cell and top end cap was affixed. The extraction cell was now ready for extraction in ASE.

C) Extraction in ASE:

The cell was loaded into an ASE instrument from Dionex corporation (Sunnyvale, Calif.) sold as ASE 100/300 for extraction at 100° C. using a pressure of 1500 psi for a 5-minute static time and using 30% flush volume for 3 cycles. Hexane was used as the extraction solvent. A 120 second purge was used to displace residual solvent after the extraction was complete. The extracts were collected in a 250 mL collection bottles (Dionex, P/N 056284). The total extraction time was about 25 min per sample.

Extraction Conditions:
Pressure: 1500 psi
Temperature: 100° C.
Heating time: 5 min
Static time: 5 min
Cycles: 3
Flush: 30%
Purge: 120 sec
Solvent: Hexane D) Evaporation:

The collected solvent/extract was evaporated in a water bath at about 70-80° C. under nitrogen gas stream. The collection bottle was further dried in an LC-30 oven (Dionex Corporation) at 75° C. for 30 min.

E) Mojonnier Extraction (Prior Art Method):

The Mojonnier extraction was done following AOAC method 996.06. The contents of the 40-mL vial containing the acid hydrolyzed samples from 1A) above were transferred to a Mojonnier extraction flask. The vial was rinsed with two portions of ethanol (5-6 mL) which were added to the Mojonnier flask. 25 mL of ethyl ether were added to the Mojonnier flask. The Mojonnier flask was shaken manually for 5 minutes. 25 mL of petroleum ether were then added to the Mojonnier flask. The flask was again shaken for 5 minutes. The Mojonnier flask was allowed to sit for 60 minutes until the organic ethers and acid layers separated and the top organic layer was free of particulates. The top layer was decanted into a pre-weighed 60 mL vial (Dionex, P/N 048784). The fat containing ethers were evaporated to dryness under a stream of nitrogen at 40-50° C. in a water bath. The evaporation was started on the low end of the range to prevent boiling and possible loss of sample. After all of the ether was evaporated, the 60-mL vials were placed in an LC-30 oven set at 75° C. to dry for 30 minutes.

Results:

Table 1 compared the results from the ASE Method (after the sample pretreatment with the sorbent/neutralizer agent) and the Mojonnier method (prior art). These results indicated both methods to provide comparable performance in terms of fat recovery or lipid %. The ASE method in conjunction with the sorbent/neutralizer agent method was much faster and was automated in comparison to the Mojonnier method of the prior art.

TABLE 1

Lipid (%) for various food samples after acid hydrolysis using ASE and Mojonnier Extraction method followed by gravimetric quantification.

| Food samples | ASE method - Resin (n = 3) | | Mojonnier method (n = 3) | |
| --- | --- | --- | --- | --- |
| | Lipid (%), average | % RSD | Lipid (%), average | % RSD |
| Corn chips | 35.25 | 0.66 | 34.90 | 0.65 |
| Mayonnaise | 75.10 | 0.45 | 74.97 | 0.33 |
| Parmesan Cheese | 29.09 | 0.80 | 29.39 | 0.98 |
| Bologna | 28.30 | 1.3 | 28.76 | 1.0 |

Example 3

This Example describes the sample preparation and extraction of pretreated acidic food sample for lipid determination using GC-MS.

Hydrolysis Procedure:

Samples of food were weighed out and placed in 40-mL vials. The amount of sample was adjusted between 0.1 and 0.5 g so that approximately 100 mg of lipid was released during hydrolysis. 0.1 g of pyrogallol was added (used to prevent oxidative losses during hydrolysis). 2 mL of internal standard solution (C19 fatty acid in chloroform) was added to the vial. 2 mL of ethanol was added and the contents were mixed. Finally 10 mL of 8 M HCl was added, the vial was mixed thoroughly. Hydrolysis proceeded for 60 min at 75-80° C. The vials were shaken constantly during the entire 60 min. All samples were hydrolyzed using these conditions regardless of the extraction procedure used (Mojonnier or ASE).

Mojonnier Procedure:

The contents of the 40-mL vial containing the hydrolyzed matrix were transferred to a Mojonnier fat extraction flask. The vial was rinsed with one 10-mL portion of $H_2O$ and two (6 mL and 5 mL) portions of reagent alcohol which were added to the Mojonnier flask. Twenty-five mL of ethyl ether were added to the Mojonnier flask. The Mojonnier flask was shaken manually for 1 minute. Twenty-five mL of petroleum ether were then added to the Mojonnier flask. The flask was again shaken for 1 minute. The Mojonnier flask was allowed to sit for 45 minutes until the water and organic layers separated and the top organic layer was free of particulates. The top layer was decanted into a pre-weighed 60 mL vial. The above procedure was repeated two more times with 15 mL of each ethers (ethyl then petroleum) instead of the 25 mL used in the first extraction.

The fat containing ethers were evaporated to dryness under a stream of nitrogen at 45-50° C. Before being placed into the water bath, the ethers were partially evaporated to prevent boiling and possible loss of sample. After all of the ether was evaporated, the 60-mL vials were placed in an oven set at 110° C. to dry for 20-30 minutes. This was done to evaporate off any residual water. The vials were then re-weighed to determine a gravimetric weight. Usually, the Mojonnier gravimetric weights are slightly higher than the other extraction methods. This is due to the ethers extracting more than just fat from the samples. Sugars and carbohydrates are among the most common interferences (depending on the sample matrix). The advantage of using the FAME analysis for fat determination is that only the fatty acids are converted to FAMEs (Fatty Acid Methyl Esters) and detected by the GC/MS. None of the interfering compounds are methylated.

Sorbent/Neutralizer Agent Pretreatment and ASE Extraction:

After acid hydrolysis was complete, the contents of the 40-mL vial were transferred to a mortar containing 30 grams of resin and 15 grams of ground ASE prep DE. The contents of the mortar were gently mixed with a pestle until a uniform mixture was obtained. The 40-mL vial was rinsed with two 2-mL portions of ethyl ether and each portion was added to the mortar. The contents of the mortar were again gently mixed with the pestle. The contents of the mortar were then added to a 100-mL Zirconium metal based ASE 350 extraction cell containing a cellulose filter and 6 grams of resin material. Five grams of resin were added to the top of the extraction cell and the extraction cell was closed. The extraction cell was placed in the ASE 350 for extraction.

ASE 350 Extraction Conditions:
Temperature: 100° C.
Static Time: 5 min
Cycles: 3
Flush: 70%
Purge: 120 sec
Solvent: Hexane After extraction on the ASE 350 (with Zirconium cells and components), the contents of the pre-weighed extraction vial were evaporated under a stream of nitrogen to dryness on the SE 500. The evaporator was set to a temperature of 70° C.

Polyacrylic Acid (Sorbent/Neutralizing Agent) Pretreatment and ASE Extraction:

The contents of the 40-mL vial containing the hydrolyzed matrix were transferred to a mortar containing 25 grams of polyacrylic acid and 15 grams of J. T. Baker diatomaceous earth (Sorbent/neutralizing agent). The contents of the mortar were gently mixed with a pestle until a uniform mixture was obtained. The 40-mL vial was rinsed with two 2-mL portions of ethyl ether and each portion was added to the mortar. The contents of the mortar were poured into a 100-mL Zirconium metal based ASE 350 extraction cell containing a glass fiber filter. The extraction cell was placed on the ASE 350 for extraction under the following conditions:

ASE 350 Extraction Conditions:
Temperature: 110° C.
Static Time: 5 min
Cycles: 3
Flush: 70%
Purge: 120 sec
Solvent: Hexane After extraction on the ASE 350 (with Zirconium cell and components), the contents of the pre-weighed extraction vial were evaporated under a stream of nitrogen to dryness on the SE 500. The evaporator was set to a temperature of 70° C.

Esterification Procedure:

After the fat residue has been extracted from the respective food matrix and taken to dryness, it was dissolved in 3 mL of chloroform and 3 mL of diethyl ether. This solution was transferred to a pressure tube. The 40-mL vial was washed a second time with chloroform and ether to ensure complete transfer of the solubilized fat to the pressure tubes (ACE Glass Inc.). The resulting chloroform/ether mixture, which contained the dissolved fats, was evaporated to dryness under a stream of nitrogen at 40° C. Once the contents of the pressure tube were dry, 2.0 mL of 12% BF3 Boron trifluoride in methanol and 1.0 mL of toluene were added to each pressure tube. The pressure tube was sealed and placed in an oven set to 100° C. for 55 min with gentle shaking every 10 minutes. The pressure tube was allowed to cool to room temperature. Five mL of $H_2O$, 2.0 mL hexane, and 1.0 g of $Na_2SO_4$ were then added to the pressure tube. The tube was shaken or vortexed for 1 minute The two layers were allowed to separate and the top hexane layer was removed and placed into a 40-mL vial containing 1.0 g $Na_2SO_4$. A second 2.0 mL portion of hexane was added to the pressure tube. The pressure tube was shaken or vortexed for 1 minute. The two layers were allowed to separate and the top hexane layer was removed and placed into the 40-mL vial containing 1.0 g $Na_2SO_4$ and the first hexane portion. A final volume of the hexane/toluene mixture was accurately measured before analysis by GC/MS. This value was used to calculate the amount of fat found in the samples. A 10× dilution was performed on all samples prepared for FAME analysis. All calculations used to determine the % recovery of fat were taken from the AOAC Official Method 996.06 section G.

GC/MS Analysis Parameters:

A RTX-Wax column (part #12423) from Restek was used in all analyses. The column was 30 meters long with an internal diameter of 0.25 mm and a film thickness of 0.25 μm. The flow rate was set to 1.4 mL/minute.

The following GC parameters were used: A 25:1 split was used. The initial Oven Temperature was held at 125° C. for 30 seconds. The oven was then heated at a rate of 7° C. per minute up to 210° C. and then held for 15 minutes. The total analysis time was 27 minutes and 40 seconds. The injection port was at 220° C. while the GC/MS interface was at 230° C.

MS conditions: The mass spectrometer was set to scan from 40 up to 550 amu (atomic mass units). The EM (electron multiplier) voltage was set to 1365 volts.

TABLE 2

Lipid (%) for various food samples after acid hydrolysis using ASE and Mojonnier method for extraction followed by FAME analysis in GC-MS.

| Food samples | ASE method - Resin based Sorbent/neutralizing agent (n = 3) | | ASE method - Polyacrylic Acid based Sorbent/neutralizing agent (n = 3) | | Mojonnier method (n = 3) | |
|---|---|---|---|---|---|---|
| | Lipid (%), average | % RSD | Lipid (%), average | % RSD | Lipid (%), average | % RSD |
| Corn chips | 29.85 | 1.1 | 29.80 | 1.2 | 30.41 | 1.2 |
| Mayonnaise | 74.25 | 0.58 | 75.00 (n = 2) | 0.04 | 75.12 | 1.2 |
| Parmesan Cheese | 26.27 | 0.84 | 26.04 | 0.67 | 26.41 | 1.1 |
| Bologna | 28.60 | 1.3 | 28.29 | 0.53 | 28.58 | 0.97 |
| Shortcake | 14.07 | 3.2 | 13.84 | 2.1 | 13.95 (n = 2) | 0.24 |

The results from Table 2 shows excellent correlation of the ASE method with the two different sorbent/neutralizing agent treatments and the Mojonnier method (Prior art method).

Example 4

Drain Method

This example describes the sample preparation and extraction of pretreated acidic food sample for gravimetric lipid determination after removing some acid from the sample container as per the Drain method of the present invention. Density of the lipids/fats is always lower than the acid so the lipids/fats should float on top of the acid layer. Draining some acid from the bottom layer of the hydrolyzed food sample helps to lower the acid content. The acid hydrolysis of food was done as mentioned in example 1. A 6-8 mL acid was removed by aspirating from the bottom layer of the acid hydrolysis of food sample prior to the sample preparation procedure described in Example 1. A PEEK tube (0.03 inch i.d., 0.062 inch o.d., Upchurch) attached to a 10 ml syringe via PEEK fittings was used for the acid removal process. The acid was The extraction condition was similar to example 1 except an ASE 300 system with stainless steel components were used for this experiment.

TABLE 3

Lipid (%) for various food samples after acid hydrolysis and acid drain using ASE and Mojonnier method for extraction followed by gravimetric quantification.

| Food samples | ASE method - Sorbent/neutralizing agent (n = 3) | | Mojonnier method (n = 3) | |
|---|---|---|---|---|
| | Lipid (%), average | % RSD | Lipid (%), average | % RSD |
| Corn chips | 35.09 | 1.6 | 34.90 | 0.65 |
| Mayonnaise | 75.34 | 1.3 | 74.97 | 0.33 |
| Parmesan Cheese | 29.43 | 0.95 | 29.39 | 0.98 |
| Bologna | 28.23 | 1.9 | 28.76 | 1.0 |

The results in Table 3 showed excellent correlation between the ASE Method (after acid removal) and the Mojonnier Method.

Example 5

As per the present invention smaller cells could be used for the acid drain method with proportionately lower amounts of sorbent/neutralizing agent materials. Another benefit of smaller cells is lower solvent usage. Therefore the use of the smaller cells would lead to lower cost per analysis. The acid hydrolysis and sample preparation was done as described in example 1. The extraction conditions are similar to example 1. A lipid content of 28.82% was achieved using a 66 mL cell using acid drained hydrolyzed Bologna samples. The recovery was comparable to the 100 mL cell as shown in example 2 and 3. The sorbent/neutralizing agent material cost can be reduced by 25-30% by implementing the drain method in a 66 ml cell versus the standard procedure of using a 100 ml cell.

Example 6

Entrapped Sorbent/Neutralizer Agent. In this example, base ($Na_2CO_3$) was entrapped in to an absorbent material (diatomaceous earth). This base-entrapped material is used for the dual purpose of absorption and neutralization of acidic sample matrix prior to solvent extraction in ASE.

Entrapped Sorbent/Neutralizer Agent Preparation:

106/g of $Na_2CO_3$ was slowly dissolved in deionized water with medium heat and stirring and the final volume was 300 mL which yielded about 3.33 M $Na_2CO_3$. A 100 mL of 3.33 M $Na_2CO_3$ was slowly added to 100 g ASE Prep DE (Dionex Corporation) for over 15-20 min with constant stirring for homogeneous impregnation. This mass was dried in an oven at 70-75° C. for 24 to 25 hrs. The moisture content of the entrapped DE was about 3% (compared to about ≤1% in the standard DE) and the capacity was about 2.4 meq/g. This appears to show that the entrapped basic material was available for neutralization reactions.

Example 7

Acid hydrolyzed Mayonnaise sample (as described in example 1) was added to a mortar containing 10 g of lightly grinded ASE Prep DE. 16 to 25 g base entrapped material from example 5 was added to the mortar and the contents were mixed with a pestle until a uniform mixture was obtained. The mass from the mortar was added to a 100 mL extraction cell containing a cellulose filter and a plug (about 5-6 g) of base entrapped DE. A plug of (about 5-6 g) of base entrapped DE was added to the top of the extraction cell and the cell was closed. The extraction cell was placed in ASE cell for extraction. Overall 26-35 g base entrapped DE and 10 g ASE Prep DE were used for sample preparation without any added resin. The extraction was done using similar conditions as described in example 1 but at 110° C. and 130° C. The collected extract was evaporated at about 70-80° C. under nitrogen stream. The collection bottle was further dried in a LC-30 oven at 75° C. for 30 min. The lipid contents were about 75.53% and 75.38% at 110° C. and 75.28% at 130° C. To check the pH, 10 mL of DI water was added to the collection bottle, shaken and mixed with the collected post extracted solvent. The water was sampled by a squeeze pipette and the pH was measured using a pH meter. The pH of the extract were near neutral (for the 26 g base entrapped DE) or slightly above neutral pH (for 35 g base entrapped DE). The above results indicated excellent utility of the method of the present invention.

What is claimed is:

1. A method of separating an organic analyte from a base in a sample comprising:
   a) sorbing a sample in a solid sorbent material having a surface comprising cationic moieties, wherein the sample includes an organic analyte and a base and wherein the cationic moieties react with the base; and
   b) contacting the sample-sorbed sorbent material with an organic solvent to extract the organic analyte;
   c) collecting the organic solvent with the extracted analyte, thereby separating the organic analyte from the base in the sample.

2. The method of claim 1, wherein the surface comprises a cation exchange media in hydronium form.

3. The method of claim 2, wherein the cationic moieties react with the base to neutralize the base.

4. The method of claim 1, wherein the surface comprises a cation exchange media in silver form.

5. The method of claim 1, wherein the surface comprises a cation exchange media in barium form.

6. The method of claim 1, wherein the surface comprises a polyacrylic acid.

7. The method of claim 1, wherein the cationic moieties are cation exchange moieties.

8. The method of claim 1, wherein the solid sorbent material comprises a material selected from diatomaceous earth, aluminum silicate, and polyacrylic acid.

9. The method of claim 8, wherein the solid sorbent material comprises diatomaceous earth.

10. The method of claim 9, wherein the surface comprises a cation exchange media in hydronium form.

11. The method of claim 1, wherein the organic analyte is a lipid.

12. The method of claim 1, wherein the organic analyte is a fatty acid.

13. The method of claim 1, wherein the sample is a food sample.

14. The method of claim 1, wherein the organic solvent is hexane.

15. The method of claim 1, further comprising maintaining the sample-sorbed sorbent material in contact with the organic solvent at a temperature ranging from 40° C. to 200° C. and a pressure of at least 100 psi.

16. The method of claim 15, wherein the temperature ranges from 80° C. to 150° C.

17. The method of claim 15, wherein the pressure ranges from 1000 to 1500 psi.

18. The method of claim 15, wherein the maintaining step is performed in an extraction chamber having a zirconium metal-based interior surface.

19. The method of claim 1, further comprising analyzing the extracted organic analyte of step (c).

20. The method of claim 19, wherein the analyzing comprises detecting the extracted organic analyte of step (c) by a technique selected from gravimetry, chromatography, or spectroscopy.

21. The method of claim 19, wherein the analyzing comprises detecting the extracted organic analyte of step (c) using gas chromatography-mass spectrometry (GC-MS).

22. The method of claim 1 in which the organic analyte is an acid sample matrix.

* * * * *